United States Patent [19]

Hermann et al.

[11] Patent Number: 5,763,697
[45] Date of Patent: Jun. 9, 1998

[54] PROCESS FOR THE NITRATION OF AROMATIC COMPOUNDS

[75] Inventors: Heinrich Hermann, Köln; Jürgen Gebauer, Troisdorf, both of Germany

[73] Assignee: Josef Meissner GmbH & Co., Köln, Germany

[21] Appl. No.: 648,890

[22] Filed: May 16, 1996

[30] Foreign Application Priority Data

Oct. 22, 1995 [DE] Germany .................. 195 39 205.1

[51] Int. Cl.$^6$ .................................................. C07C 205/00
[52] U.S. Cl. ................................................ 568/939; 568/940
[58] Field of Search ............................... 568/939, 940

[56] References Cited

U.S. PATENT DOCUMENTS 3,092,671 6/1963 Humphrey et al. .
4,973,770 11/1990 Evans .
5,313,009 5/1994 Guenkel et al. .

*Primary Examiner*—Samuel Barts
*Attorney, Agent, or Firm*—Cohen, Pontani, Lieberman, Pavane

[57] ABSTRACT

The selective introduction of a nitro group into an aromatic compound by mixtures of nitric acid and sulphuric acid, wherein the aromatic compound to be nitrated is conveyed to a central driving jet of the acid mixture in such a way that it surrounds the mixed acid jet.

9 Claims, 1 Drawing Sheet

PROCESS FOR THE NITRATION OF AROMATIC COMPOUNDS

BACKGROUND OF THE INVENTION

1. Field of the Invention

This invention relates to a continuous process for the nitration of mononuclear aromatic compounds in mixed acid in a two-phase liquid system.

2. Description of the Related Art

The nitration of aromatic compounds like benzene; toluene and chlorobenzenes, etc. to mononitro or dinitro derivatives is technically mainly carried out in a continuous way by mixing nitric and sulphuric acid (mixed acid) and the aromatic compounds to be nitrated. The solution of mixed acids which is used for nitration generally consists of 20–30% nitric acid, 55–65% sulphuric acid and 5–25% water. In general, the nitration of these aromatic compounds is performed in a heterogeneous two-phase liquid system. The actual composition of the mixed acid employed is adapted to the properties of the aromatic compound which is to be nitrated in such a way that a spent acid of about 70% sulphuric acid, 29–30% water and 0–1% nitric acid is obtained. After a residence time which depends on the manufactured nitroaromatic compound, the two-phase nitration emulsion is separated and the product as well as the used up mixed acid (spent acid) are each either conveyed to their purification (product and spent acid) or to reconcentration (spent acid).

Nitration essentially proceeds in the acid phase. The aromatic compound to be nitrated has to be transferred from the organic phase to the acid phase where reaction to the desired nitroaromatic takes place in the presence of an excess of nitric acid. Thus, the conversion per unit of time not only depends on the kinetic parameters of reaction but also on the efficiency of mass transfer from the organic to the acid phase.

The large interfacial area between the organic and acid phase needed for a rapid mass transfer is normally obtained by vigorous stirring. In the resulting emulsion either the organic phase is dispersed in the acid phase or the acid phase in the organic phase. The type of emulsion depends on the ratio of phases and on the aromatic compound to be nitrated. In continuous nitrations, the nitration is mainly performed in a cascade of constant flow stirred tank reactors (CFSTR) with complete back mixing.

In this case nitration takes always place in each vessel at constant sulphuric and nitric acid concentrations and with a constant rate of conversion.

The acid concentrations in the mixed acid and those for the individual stirred tank reactor, and thus the rate of conversion, are selected in such a way that only the desired nitro compound (e.g. nitrobenzene from benzene or mononitrotoluene from toluene) is formed as rapidly as possible and that further reaction to the respective dinitro compound is as slow as possible. Thus the selectivity of a desired conversion is kept very high. For benzene and toluene, for instance, nitration is carried out in acids in which the sulphuric acid concentrations are about 70% and the nitration temperature is as low as possible (e.g. benzene 55° C. and toluene 35° C.) in order to maintain high selectivity. If nitration is carried out at higher temperatures, for instance in adiabatic nitration at around 120°–135° C. for benzene (U.S. Pat. No. 4,091,042 "Adiabatic manufacture of nitrobenzene"), then the sulphuric acid concentration in the nitrating acid (for instance in a cascade of constant flow stirred tank reactors) must be reduced to such an extent that the selectivity is ensured at a given residence time in the reactor (for instance up to 65% sulphuric acid in the actual nitrating acid).

Besides the acidity of the nitrating acid (K. Schofield in "Aromatic Nitration", Cambridge University Press 1980, Cambridge) and the temperature, other factors which influence the selectivity are of course the concentration of the nitric acid as well as the residence time of the nitration mixture in the reactor.

If continuous nitration is performed in a tubular reactor by mixing the product to be nitrated with a mixed acid consisting of high nitric acid and sulphuric acid concentrations and a low water content, the selectivity for the desired product is reduced, particularly if the reactants are not mixed homogeneously in an optimal way. With typical mixed acids, the initially formed mononitro compounds will be nitrated further (for instance, mononitrobenzene to dinitrobenzene), particularly at the beginning of nitration in the tubular reactor when the acidity and the nitric acid concentration in the mixed acid are still high. Said loss in selectivity can be avoided if reaction proceeds either with mixed acids whose acidity is only slightly higher when compared to optimal nitrating acids so that the rate for further nitration of the initially formed product is slow, or if by fast conversion of the aromatic compound to be nitrated—present in excess—the acidity in the nitrating mixture is quickly reduced by rapid consumption of nitric acid and by the formation of water. This ensures that the selectivity can be maintained. The application of standard mixing techniques such as e.g. the mixing in a stirred tank reactor or the injection of the material to be nitrated into a turbulent jet of acid as already successfully applied in nitration of alcohols (glycerine or glycol) as described in DE-PS-1 039 049, is considered insufficient for achieving the required high dispersion of the material to be nitrated in the mixed acid, particularly for the application in large-scale industrial plants in which large mass streams have to be mixed per unit of time (see U.S. Pat. No. 4,973,770).

In order to meet the requirement of maintaining a high selectivity during nitration in a tubular reactor and to minimize the formation of by-products (e.g. formation of dinitrobenzene, nitrophenols and other products of oxidation during the nitration of benzene to mononitrobenzene), attempts were made to disperse the material to be nitrated in the acid phase as quickly as possible in form of a homogeneous, highly dispersed emulsion. This can be achieved by mixing the reactants in a centrifugal pump as described in U.S. Pat. No. 3,092,671, or by using special nozzles as described in U.S. Pat. No. 4,973,770, or by applying a greater number of jet mixers in a special arrangement as described in U.S. Pat. No. 4,994,242 and U.S. Pat. No. 5,313,009. These measures were to yield an optimal mass transfer (for instance, transfer of benzene from the organic phase to the acid phase) by a rapid creation of a large interfacial area between the acid and the organic phase in order to achieve high conversion of the product to be nitrated at the beginning and to bring about a rapid reduction of the high acidity and the high nitric acid concentrations in the starting mixed acid.

It is generally known, however, that the formation of unwanted by-products cannot be reduced to a minimum by dispersing the product to be nitrated in a mixed acid of high sulphuric and nitric acid concentrations which favor a rapid further nitration of the formed mononitroaromatic. Particularly at the beginning of a nitration, the newly formed nitro compound (e.g. mononitrobenzene), being dissolved up to its limit of saturation in the nitrating acid mixture which is still highly acidic and having a high nitric acid concentration, will be rapidly nitrated further, oxidized and/or destroyed.

Dispersion of the mixed acid in the product to be nitrated in a special mixing device, as also described in U.S. Pat. No. 4,973,770, does not offer an improvement. Also in this case, highly reactive fresh mixed acid with low selectivity is in contact with the mononitro product. In each droplet the originally formed nitro compound is dissolved up to its saturation point from the beginning, and it is subject to further nitration as long as acidity and nitric acid concentration are not yet reduced by the water - formed during nitration - to the level of the spent acid with its high selectivity. Apart from that, the dispersion of the acid in the organic phase with high phase ratios of acid phase/organic phase (5–10:1, as for instance in adiabatic nitration of benzene) involves the great additional risk that the organic phase in the described reaction chamber is rapidly washed out due to the great excess of acid phase. The acid phase will accumulate and form the homogeneous phase. This leads to completely uncontrollable and undefined emulsifying conditions for the phases. Thus, the risk of by-product formation is not reduced but considerably increased.

The formation of unwanted by-products by nitration can only be avoided to the greatest possible extent—also at the beginning of nitration—if nitration is carried out all the time in an almost completely used-up mixed acid (spent acid) as for instance in batch nitration of benzene or toluene to form the respective monoderivatives.

In batch nitration, the mixed acid and the aromatic compound to be nitrated are not mixed in stoichiometric proportion. The mixed acid is stepwise added to the aromatic compound in the reaction tank in such a way that from the beginning nitration always takes place in a spent acid of the lowest possible acidity and nitric acid concentration.

SUMMARY OF THE INVENTION

It is an object of this invention to provide a process for selective introduction of one nitro group into an aromatic compound with mixtures of nitric acid and sulphuric acid (mixed acid) in a tubular reactor without back mixing that avoids formation of unwanted by-products during nitration.

The invention provides a method for mixing the aromatic compound to be nitrated with a jet of mixed acid in such a way that the aromatic compound- surrounds and envelopes the central acid jet. Among others, benzene, toluene, xylenes, chlorobenzenes, dichlorobenzenes, chlorotoluenes, nitrobenzene and mononitrotoluenes can be used as aromatics. Besides that, all aromatic compounds, the nitration products of which are liquid up to 100° C. can be used as mononuclear aromatics.

Conditions similar to those in batch nitration of aromatic compounds to mononitroaromatic compounds can also be adjusted for continuous nitration in a tubular reactor in such a way that the mixed acid is only partially distributed in the aromatic compound to be nitrated and at an optimal droplet size, that means, by microturbulences created at the boundary surfaces of both phases in a specially designed mixer (FIG. 1). In this way only the mixed acids which are in direct contact with the aromatic compound react almost completely to form spent acid so that a further reaction of the dissolved product, e.g. mononitrobenzene, can only occur slowly. When fresh mixed acid which has not yet been impaired by the nitrated product is added to the said produced spent acid, and both are continuously mixed, the result will always be a nitrating acid the composition of which largely corresponds to that one of the spent acid.

The best method to mix low-viscous aromatic compounds to be nitrated (e.g. benzene) with a mixed acid in the described way consists in utilizing the nitrating acid (acid phase) as driving jet as for instance in an injector in which the axially inflowing product to be nitrated (organic phase) surrounds this central jet completely.

DETAILED DESCRIPTION OF THE PRESENTLY PREFERRED EMBODIMENTS

Figure 1:
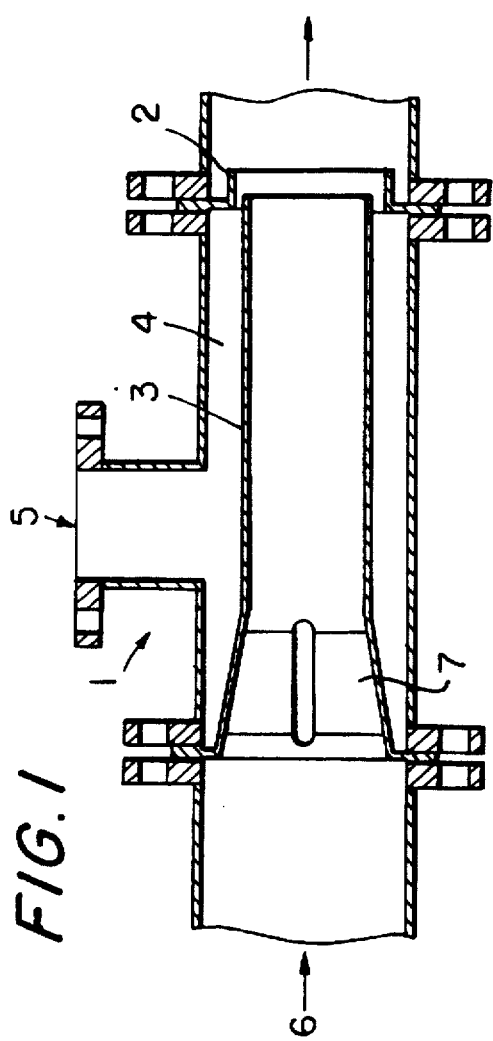
FIG. 1 a schematic section through the mixing device relating to this invention.

FIG. 1 shows the annular-slit mixer or annulus mixer (1) as per the present invention designed as a modified injector consisting of a mixing tube which in this case is designed as an inserting ring (2), an internal tube (3), an intermediate annular space or annulus (4) with feeding end (5) for the aromatic compound to be nitrated, an inlet (6) for the nitrating acid with baffles (7), located inside the internal tube, and of a part of the subsequently arranged tubular reactor (8).

Figure 2:
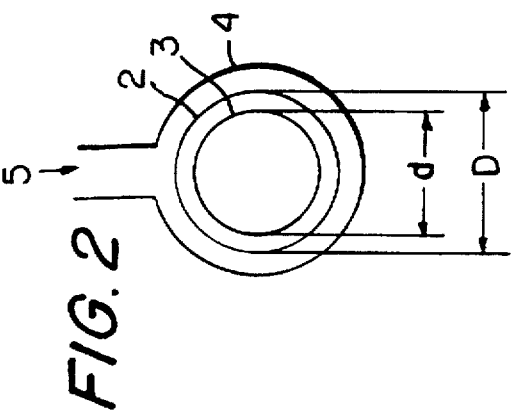
FIG. 2 is a schematic top view of the outlet side of the mixing device as disclosed in FIG. 1.

An initial dispersion of the acid phase in the organic phase is achieved when the ratio of flow velocities V1/V2 (acid phase/organic phase) of both phases to be mixed is one and greater than one and the ratio of the driving jet diameter (d) with respect to the entire diameter of the mixing tube (D) is at least 0.7 up to 0.98 (FIG. 2) and the flow velocities of both phases reach Reynold's numbers of greater than 5000.

The respective phase ratio between mixed acid and aromatic compound is 1:2 up to 10:1, and the respective ratio between the velocity of the central driving jet of mixed acid and the enveloping aromatic phase ranges between 1 and 10:1.

By baffles (7) inside the central tube (3) or by other means, the mixed acid, the density and viscosity of which are higher than the density and viscosity of the aromatic to be nitrated, is also provided with a tangential component in addition to the co-current flow. This additional tangential component causes the central mixed acid jet to rotate. The ring of the organic phase which has a lower density and viscosity in comparison to the mixed acid can additionally be treated in a similar way. Thus, an even more rapid dispersion of the central jet in the surrounding organic phase and vice versa is achieved by centrifugal force. When both phases are brought together in the described way the central mixed acid jet reacts from outside to inside. At first, only at the interfacial area between acid and organic phase reaction starts, nitric acid will be consumed and water will be formed. Only the acid phase in contact with the organic phase is saturated with the product, and the acid composition of this acid phase corresponds to that one of the spent acid.

During the course of reaction still fresh mixed acid is continuously added from the central part of the jet to this interfacial area, thus fortifying the spent acid between fresh mixed acid and organic phase to such an extent that the conversion of unreacted organic compound continues.

Thus, formation of by-products is reduced to a minimum (for instance the formation of dinitrobenzene due to further reaction of the initially produced mononitrobenzene or the formation of phenols due to oxidation of the aromatic compound to be nitrated or of the product due to an excess of nitric acid in the acid or organic phase).

An especially important advantage consists in this rapid inverse mixing of acid in the organic phase at the beginning of nitration if the rate of nitration at the interfacial areas between organic and acid phase is equal to or greater than the mixing velocity as, for instance, in the nitration of benzene and toluene during which up to 80% or more of the main conversion takes place within split seconds. Consequently, when a homogeneous dispersion of the aromatic compound to be nitrated and of the formed mononitro compound is obtained, then the acidity and the nitric acid content in the original mixed acid, e.g. in the total amount, has been reduced to such an extent that there is only a slight formation of unwanted by-products during the residence time which is still required for complete conversion of the residual nitric acid.

The described design of mixing devices is preferred for the nitration of aromatic compounds like, for instance, benzene, toluene, xylene and chlorobenzene in those cases where the phase ratio between both phases differs considerably from 1, as for instance in the case of adiabatic nitration of benzene where the ratio between acid phase and organic phase is about 5–10:1, preferably 7–8:1. This holds also for isothermal reaction when the phase ratio between acid and organic phase is increased due to recycling of spent acid or due to the use of partially reconcentrated spent acids which have a sulphuric acid concentration of between 85% and 92% after reconcentration. The great excess of acid phase can be used as central driving jet. When mixing is finished the said acid phase forms the homogeneous phase in which the aromatic compound to be nitrated is dispersed together with the product.

After both reactants have been mixed in the mixing device according to invention (see FIG. 1) the heterogeneous, two-phase nitrating mixture can be fed into a tubular reactor without back mixing or into a cascade of constant flow stirred tank reactors for complete conversion of the aromatic to be nitrated and for conversion of the still remaining nitric acid in such a way that the optimal dispersion, yielded in the above described mixer, is maintained by turbulence and/or with additional use of static mixing elements or by agitation if stirred tank reactors are used. In the process according to invention, the mixed acid is composed of nitric acid 20–30% by weight, sulphuric acid 55–65% by weight and water 5–25% by weight. A modified design of the invention uses a mixed acid composed of nitric acid 2.5–8.5% by weight, sulphuric acid 58–70% by weight and not less than 25% by weight of water.

Figure 3:
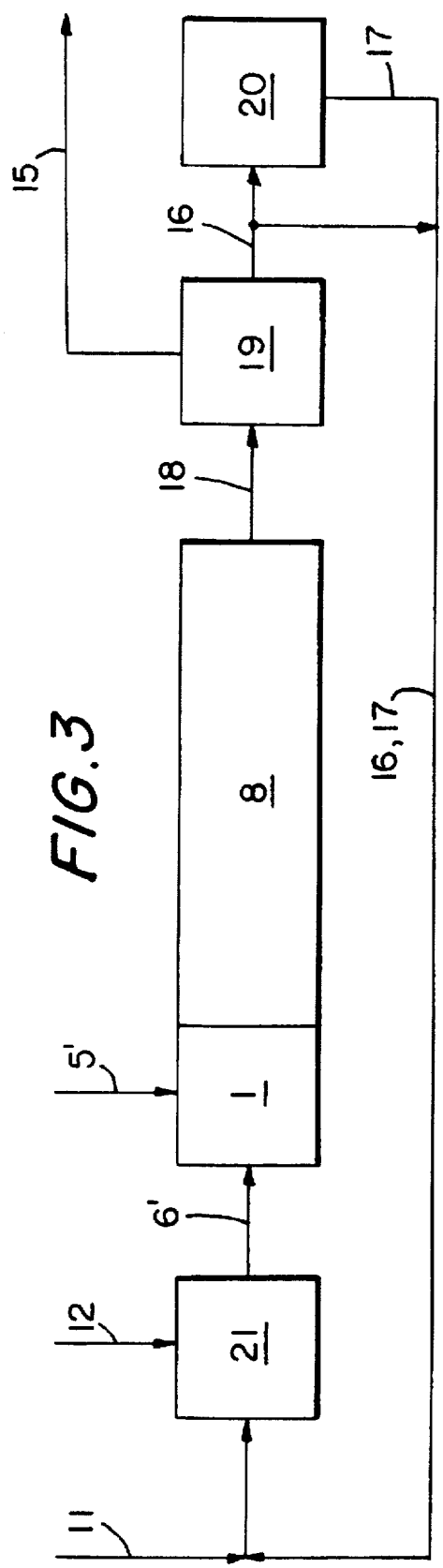
FIG. 3 a schematic view of a plant for the manufacture of nitrobenzene pursuant to this invention.

In a plant for the manufacture of nitrobenzene (FIG. 3) equipped with a tubular reactor without back mixing (8), used as residence time section for instance in adiabatic processes for nitration of benzene, a mixed acid (6) is prepared which has a composition of 2.5–8.5% nitric acid, 58–70% sulphuric acid and not less than 25% water. Preferably a mixed acid composed of 3–5% nitric acid and 63–68% sulphuric acid is used that yields a spent acid of 62–71% sulphuric acid after finished nitration. This is achieved by mixing sulphuric acid 68–72% (17) which comes from a plant for reconcentration of spent acid (20), e.g. obtained from an adiabatic nitration of benzene or by mixing sulphuric acid 96% (11) and recycled spent acid (16) with nitric acid 65% or 98% (12) in the mixer (21).

This mixed acid being produced either in stirred vessels or by in-line mixing in a mixing device as per invention or by application of other static mixing elements, is brought to the desired reaction temperature and used as driving jet for the mixing device (1). The benzene to be nitrated (5), used in excess of about 10–15% referred to the nitric acid applied, is brought in contact with this mixed acid prepared in mixer (21) in the mixing device (1) according to the invention (see FIG. 1).

Due to the intimate inverse mixing of both components (for instance, benzene and mixed acid) the major part of benzene is already converted to the desired product nitrobenzene after leaving the mixing device (1). The tubular reactor (8) after the mixer (1) is designed in such a way that the emulsion produced in the mixing device (1) is maintained and the residence time in the reactor is long enough to consume even the rest of nitric acid which is still present in the acid phase after the mixing device (1).

The nitration mixture (18) which leaves the tubular reactor (8) is separated in a static or in a dynamic separator (19). The separated nitrobenzene which still contains about 5–10% of benzene is conveyed to a washing stage in order to remove the traces of dissolved nitric acid, nitrous oxides and nitro phenols, followed by stripping/drying or distillation to eliminate the residual benzene and water. The resulting spent acid (16) is conveyed to a purification and reconcentration stage (20) to remove the water which was formed during nitration and brought in along with the nitric acid. It is subsequently recycled to nitration in form of partially purified sulphuric acid (17). A modified embodiment of this invention is to introduce the mixture of the aromatic compound to be nitrated, its nitro compound, and the mixed acid after it has left the mixing device (1) into a cascade of constant flow stirred tank reactors in order to finish nitration.

Mononitrobenzene which was manufactured according to the invention and in which the benzene and the mixed acid are dispersed into one another in a mixing unit as per invention, contains less than 200 ppm dinitrobenzene and not more than 2000 ppm nitrophenols (2.4 dinitro phenol, 2.6 dinitro phenol and picric acid). The exact amount depends to a high degree on the reaction temperature. The picric acid content of the nitrophenol mixture varies between 10–50% depending on the acidity of the mixed acid used and the nitration temperature.

We claim:

1. A process for the selective introduction of a nitro group into an aromatic compound by contacting said aromatic compound with a mixture of nitric acid and sulphuric acid (mixed acid), wherein said aromatic compound to be nitrated is conveyed to a central driving jet of mixed acid in such a way that it surrounds said mixed acid jet.

2. The process of claim 1 wherein the phase ratio between mixed acid and aromatic ranges from 1:2 up to 10:1.

3. The process of claim 2 wherein said central driving jet of mixed acid and said surrounding aromatic phase to be nitrated each are propelled at a velocity wherein the ratio of said velocities ranges from 1:1 up to 10:1.

4. The process of claim 3 wherein said driving jet of mixed acid is turbulent and a tangential component is superimposed on the flow direction of said turbulent driving jet of mixed acid.

5. The process of claim 4 wherein said aromatic compound to be nitrated is selected from the group consisting of benzene, toluene, xylene, chlorobenzene, dichlorobenzene, chlorotoluene, nitrobenzene or mononitrotoluene.

6. The process of claim 5 wherein said mixed acid comprises:
20–30% by weight of nitric acid
55–65% by weight of sulfuric acid, and 5–25% by weight of water.

7. The process of claim 6 wherein said mixed acid is comprises:

2.5–8.5% by weight of nitric acid

58–70% by weight of sulfuric acid, and not less than 25% by weight of water.

8. The process of claim 6 wherein a mixture consisting of said aromatic compound to be nitrated, its nitro compound and the mixed acid is fed into a tubular reactor without back mixing in order to complete nitration.

9. The process of claim 6, wherein a mixture consisting of said aromatic compound to be nitrated, its nitro compound and the mixed acid is introduced into a stirred tank reactor to complete nitration.

* * * * *